United States Patent

Popadiuk et al.

[11] Patent Number: 5,556,426
[45] Date of Patent: Sep. 17, 1996

[54] PTFE IMPLANTABLE TUBULAR PROSTHESES WITH EXTERNAL COIL SUPPORT

[75] Inventors: Nicholas Popadiuk, Hillsborough; Horng-Ban Lin, Pompton Lakes; Richard J. Zdrahala, Montville, all of N.J.

[73] Assignee: Meadox Medicals, Inc., Oakland, N.J.

[21] Appl. No.: 284,904

[22] Filed: Aug. 2, 1994

[51] Int. Cl.⁶ .................. A61F 2/06; A61F 2/04
[52] U.S. Cl. .................. 623/1; 623/12
[58] Field of Search .................. 623/1, 11, 12; 606/151–158, 194, 195; 600/36

[56] References Cited

U.S. PATENT DOCUMENTS

| Re. 31,618 | 7/1984 | Mano et al. . |
| 3,105,492 | 10/1963 | Jeckel . |
| 3,479,670 | 11/1969 | Medell . |
| 3,882,845 | 5/1975 | Bucalo .................. 128/1 R |
| 4,306,318 | 12/1981 | Mano et al. . |
| 4,550,318 | 11/1985 | Seiler, Jr. et al. . |
| 4,747,849 | 5/1988 | Galtier . |
| 4,850,999 | 7/1989 | Planck . |
| 4,973,609 | 11/1990 | Browne . |
| 5,061,276 | 10/1991 | Tu et al. .................. 623/1 |

FOREIGN PATENT DOCUMENTS 0022792 6/1972 Japan .

OTHER PUBLICATIONS

R. Guidoin, et al, "Expanded Polytetrafluoroethylent Arterial Prostheses in Humans: Histopathological Study of 298 Surgically Excised Grafts," *Biomaterials*, 14, pp. 678–693 (1993).

Primary Examiner—Debra S. Brittingham
Attorney, Agent, or Firm—Hoffmann & Baron

[57] ABSTRACT

A flexible implantable luminal device is disclosed, which is made from a porous cylindrical tube manufactured from extruded fluoropolymer. A fluoropolymer filament is wrapped helically around the external surface of the tube. The filament is fused to the tube to form a unitary composite structure by heating the wrapped tube to a temperature above the melting points of the fluoropolymers. The resulting composite is a radially reinforced flexible luminal prosthesis suitable for implantation, particularly, as a vascular graft or endoprosthesis. Also disclosed is a method for manufacturing the prosthesis.

14 Claims, 3 Drawing Sheets

FIG-4

PTFE IMPLANTABLE TUBULAR PROSTHESES WITH EXTERNAL COIL SUPPORT

BACKGROUND OF THE INVENTION

1. Field of the Invention

The present invention relates generally to thermoplastic composite structures suitable for surgical implantation as tubular prostheses and to methods of making such implantable tubular prostheses. In a specific aspect, the present invention relates to externally reinforced fluoropolymer composite tubular structures formed by polymer extrusion methods.

2. Description of the Related Art

An ideal implantable tubular prosthesis will closely approximate the physical and physiological characteristics of normal body tissue. A variety of luminal prosthetic materials and structures have been manufactured in attempts to produce just such a prosthesis. While significant progress has been made along many of the parameters defining ideal prostheses, no material or structure has heretofore produced truly ideal performance.

An implantable tubular prosthesis should be biocompatible, resisting degradation or encapsulation by adjacent tissues, and causing neither mutagenic nor allergic responses in the organism. In addition, the prosthesis must be flexible and strong, as well as resistant to tearing, puncture, aneurism and collapse. Among the luminal devices used as conduits for repairing or replacing natural tubular structures are those which serve as conduits for blood, such as endovascular prostheses and vascular grafts. These luminal devices, besides requiring the above-mentioned properties, must also avoid inciting excessive thrombotic responses in the blood they convey.

It has been found that prostheses which effectively avoid the formation of thrombus develop endothelial linings or neointima. The neointima arise through the deposition of adhesion glycoproteins on the interior surface followed by fibrin deposition and endothelial cell migration and growth. The neointimal lining is desirably limited in depth, but commonly exceeds normal epithelial growth limitations (e.g., depth of fibrin layer, confluence of sheet) to, in the case of smaller prostheses, constrict or eliminate the lumen of the synthetic portion of the blood vessel.

Among the measures observed to reduce such vascular compromise, the introduction of pores into the walls of the prosthesis has proven effective. In larger diameter prostheses, such pores are often a product of the woven material used as the prosthetic structure. In smaller vessels, woven materials have been found to be less desirable, and preferred materials include porous fluoropolymers. The porosity of these materials has been found to be a critical factor in their utility as implantable prostheses, since ingrowth of tissue onto the walls of the prostheses directly improves their biocompatibility.

In addition to possessing antithrombogenic characteristics on the internal surface of the tubular prostheses, endovascular conduits and vascular grafts must be sufficiently compliant to withstand the hemodynamics of the body, as well as being resistant to leakage upon implantation. It is very important that the walls of the device possess sufficient radial strength to remain patent (open), thereby allowing proper blood flow, yet also be kink resistant to allow handling and manipulation by the surgeon who implants it.

Fluoropolymer tubes used as flexible implantable devices, e.g., vascular grafts, however, demonstrate a variety of physical limitations directly attributable to the microstructure of the materials and resulting from their method of formation. Most fluoropolymer tubes are extruded, leading to a node-fibril microstructure in the polymer, with the majority of the fibrils oriented in the direction of extrusion, namely axially or longitudinally. Because of this longitudinal bias inherent in the tubes' microstructure, the tubes are relatively strong in the longitudinal or axial dimension. But by the same token the tubes tend to be relatively weak in the lateral or radial dimension. Furthermore, because of the longitudinal orientation of the microfibrils, extruded flexible fluoropolymer tubes designed as implantable prostheses tend to kink, pinch, or collapse when they are bent. The longitudinal orientation of the fibrils produced by extrusion also tends to manifest as a defect when the prosthesis is sutured into place, commonly tearing along the axial dimension at the point where the suture pierces the tube and exerts its tensional effect. Tearing then propagates along the longitudinal direction, causing the loss of structural integrity. According to these physical and mechanical criteria, conventional fluoropolymer prostheses are unacceptably deficient in comparison to normal vascular tissue, which is notably tough but pliable.

Numerous attempts have been made to improve the radial tear strength and to reduce the mechanical deformation of fluoropolymer vascular prostheses. For example, a variety of methods rely on the use of laminated composite materials. Other methods call for controlling the orientation of microfibrils or other microstructure, in order to enhance the radial strength of the extruded fluoropolymer.

Other methods known in the art for improving the toughness and flexibility of fluoropolymer tubes involve adding radial strength by modifying the structure of the prosthetic tube. Such modifications have usually involved adding structural support that is of a magnitude larger than that of the microfibrils. Typically, these methods have employed the use of materials other than fluoropolymers and which have different physical characteristics, particularly greater elasticity. These methods have also often provided a framework of supporting ribs or coils oriented radially or circumferentially rather than longitudinally, additional layers of alternative materials, or both ribs and layers in combination.

For example, a method described in U.S. Pat. No. 4,550,447, provides for extruding a porous fluoropolymer tube and then cutting circumferentially or helically into the external wall of the tube and heating the tube to cause ribs or helices to form. The resulting ribs or helices tend to have a less porous microstructure.

U.S. Pat. No. 5,061,276 describes a vascular graft made from a porous tetrafluoroethylene tubing having a wrapping of elastic fibers applied at various angles oblique to the longitudinal axis and exerting varying tensions upon the tubing.

Materials using helical support measures include those described in U.S. Pat. Nos. 4,306,318 and Re. 31,618. These patent documents describe organic prostheses made from polytetrafluoroethylene tubing and having elastic filaments wrapped around the exterior of the tube in a helical orientation.

U.S. Pat. No. 3,479,670 also describes tubular surgical prostheses. The tubular portions are described as mesh fabric tubes made from tetrafluoroethylene polymer or polyethylene terephthalate. The mesh tubes are wrapped with a low-melting polypropylene monofilamentous helix fused to the outside surface of the tube.

U.S. Pat. No. 4,747,849 describes an esophageal prosthesis. The tubular prosthesis is described as having a flexible inner wall and a rigid outer wall, with a helical filament or yarn of relatively elastic material positioned between the two walls. Materials for the prosthesis include polytetrafluoroethylene polymers, silicone polymers, and, preferably, polyurethane. The prosthesis has a circular cross-section in the central portion, while being elliptical at the orifices at either end.

U.S. Pat. No. 4,850,999 discloses implantable prostheses including a tube and a braided reinforcing component. The hose may be woven or knit or may be of a synthetic resin, including expanded polytetrafluoroethylene. The braid may be a braid of metal filaments or filaments of a synthetic resin. The braid is described as affixed to either the inner or outer surface of the tube by glue or adhesive, or by embedding the braid between two layers of material.

From the previous discussion it is apparent that both conventional textile prostheses as well as PTFE prostheses have respective benefits and disadvantages, but neither offers properties which solve all of the aforementioned problems, and especially the kink, crush and tear resistance properties which are so desirable in synthetic prostheses of the described type.

None of the aforementioned patents disclose unitary implantable prostheses made from a porous fluoropolymer tube reinforced with an external fluoropolymer helical support to provide excellent hemocompatibility and resistance to tearing and deformation. Other measures have generally been needed, requiring the addition of adhesives or heterogeneous reinforcing materials with less desirable characteristics, or requiring precise and complex mechanical manipulation of an extruded tube. These attempts have also failed to produce uniform and integral reinforced prostheses possessing the desired properties described above.

Therefore, it would be a significant advance in the art to overcome the above-described difficulties associated with reinforcing extruded fluoropolymer implantable prostheses, in a manner obviating the use of less biocompatible materials or expensive and difficult mechanical methods of modification of extruded fluoropolymer tubes.

The present invention solves the disadvantages inherent in the prior art by providing a method for manufacturing implantable prostheses from extruded flexible fluoropolymer tubes with fluoropolymer-based reinforcing structures, taking advantage of the excellent biocompatibility of fluoropolymers without compromising the porosity of the prosthesis important for its utility. The present invention also provides implantable prostheses that exhibit superior physical characteristics, such as resistance to suture-induced tears and various types of deformations induced by extraneous stresses generated during implantation as well as in situ.

Accordingly, it is an object of the invention to provide a method of manufacturing an improved, radially reinforced implantable prosthesis.

It is a further object of the invention to provide an improved implantable tubular prosthesis which overcomes the above-described deficiencies of the prior art practice.

Other objects and advantages of the present invention will be more fully apparent from the ensuing disclosure and appended claims.

SUMMARY OF THE INVENTION

In one aspect, the present invention relates to an implantable tubular prosthesis or luminal device having improved resistance to mechanical deformation and disruption, and a method for its manufacture. The implantable tubular prosthesis includes a flexible, porous, tubular component, made from fluoropolymer, and a support component including at least one flexible fluoropolymer filament wrapped helically around the external wall of the tube and fused to the tube so as to provide a unitary biocompatible prosthesis.

A variety of fluoropolymer compositions are useful according to the invention, including single and alloyed fluoropolymers manufactured according to processes known in the art. Such fluoropolymers include polymers of tetrafluoroethylene, fluorinated ethylene-propylene copolymers, tetrafluoroethylene copolymers with ethylene, tetrafluoroethylene copolymers with perfluorovinyl ethers, and mixtures thereof. The preferred fluoropolymer is polytetrafluoroethylene.

The tubular portion of the prosthesis may be manufactured according to methods known in the art, preferably by extrusion methods. The temperature of extrusion is preferably below the crystalline melting point of the fluoropolymer.

The support component of the tubular prosthesis may be made from a single fluoropolymer or an alloy of fluoropolymers selected from among those described as useful for making the tubular portion. The support filament(s) of the prosthesis may be made according to methods known in the art, preferably by extrusion methods and preferably extruded at a temperature below the crystalline melting point of the fluoropolymer. The support filament(s) are preferably monofilament, but may each be a braid of two or more smaller filaments.

The filament portion includes at least one filament wrapped helically around the tubular portion. The filament may be continuous, running the length of the prosthesis or may be discontinuous, being formed of several filament portions each running along a segment of the luminal device. The filament portions, if discontinuous, may be consecutively aligned without overlap along the length of the device, or may overlap.

The filament portion may comprise two or more filaments wound either in the same orientation as the others or at an alternative orientation such as forming an opposing helix to form a braid pattern in the device.

The composite prosthesis is formed by first expanding the tube by stretching the tubular component in an axial and/or radial dimension. Then the filament(s) of the support component is/are wound around the tube in a helical configuration. The assembly is then controllably heated to a temperature above the crystalline melting point of the fluoropolymer to sinter the assembly, thereby fusing and uniting the assembly into a reinforced tubular structure for use as a vascular prosthesis. It is preferred that both the support component and the tube component be made of the same fluoropolymer.

The flexible implantable luminal device may comprise a vascular prosthetic device, such as a vascular graft or an endovascular prosthetic device.

For a better understanding of the present invention, reference is made to the following description made in conjunction with the figures, the scope of which is defined in the claims.

DETAILED DESCRIPTION OF THE PREFERRED EMBODIMENTS

In one aspect, the present invention relates to implantable tubular prostheses having improved resistance to mechanical deformation and disruption and a method for their manufacture. The implantable tubular prostheses are manufactured from a porous cylindrical tubular component, made from fluoropolymer, and a support component including helical wrapping of filamentous fluoropolymer around the external wall of the tube and fused to the tube so as to create a unitary biocompatible prosthesis.

Figure 1:
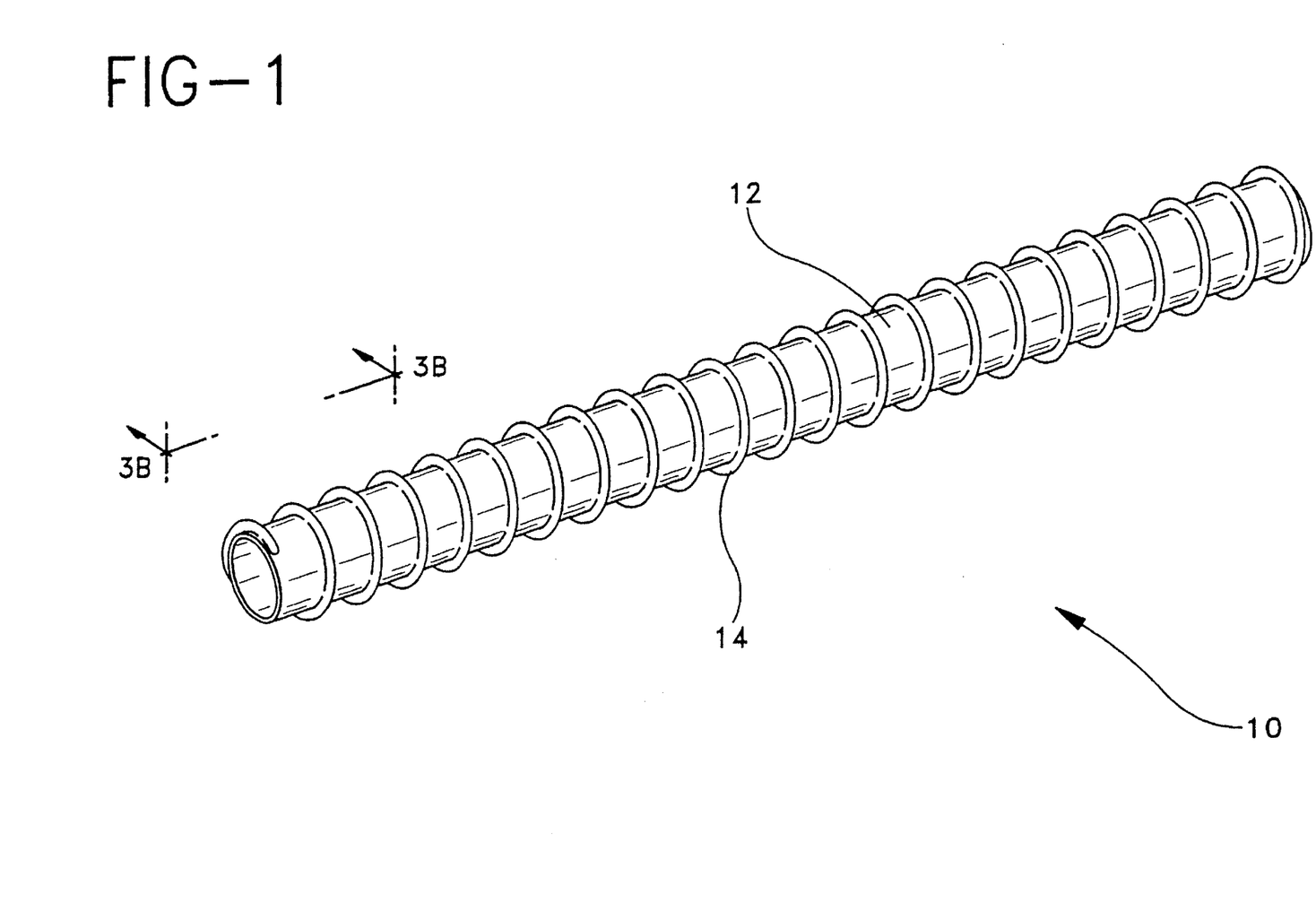
FIG. 1 illustrates the flexible implantable luminal device of the invention, in perspective view.

Referring to the Figures, an idealized illustration of a preferred embodiment of the implantable reinforced luminal device of the invention is provided in FIG. 1. The luminal device of the invention 10 comprises a porous cylindrical tubular component 12 and a filament component 14 which has been wrapped helically around the tubular component 12 and fused thereto.

Figure 2:
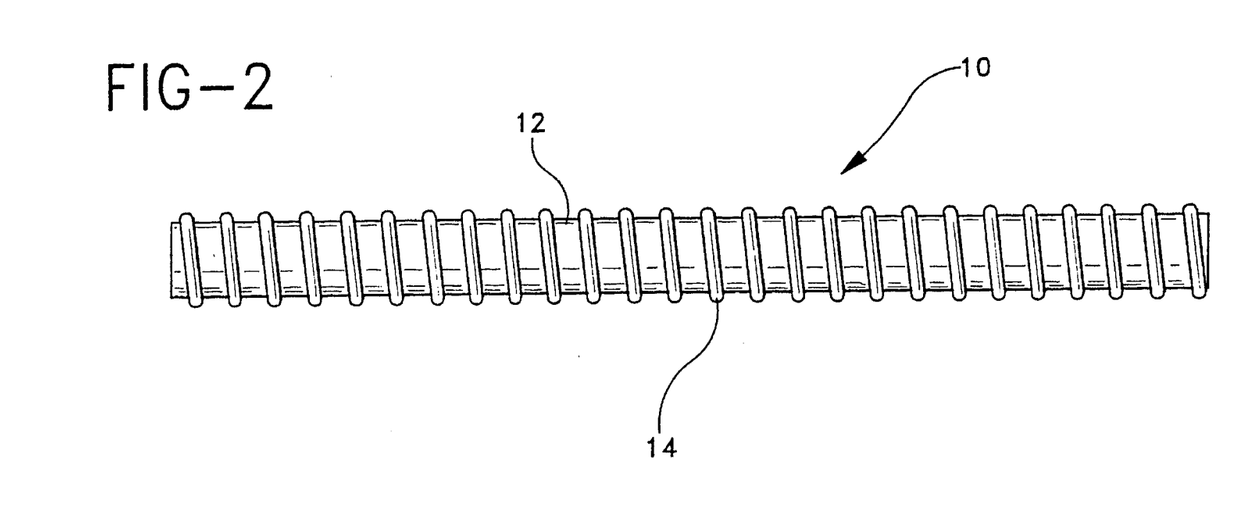
FIG. 2 illustrates the flexible implantable luminal device of the invention viewed from the side.
Figure 3A:
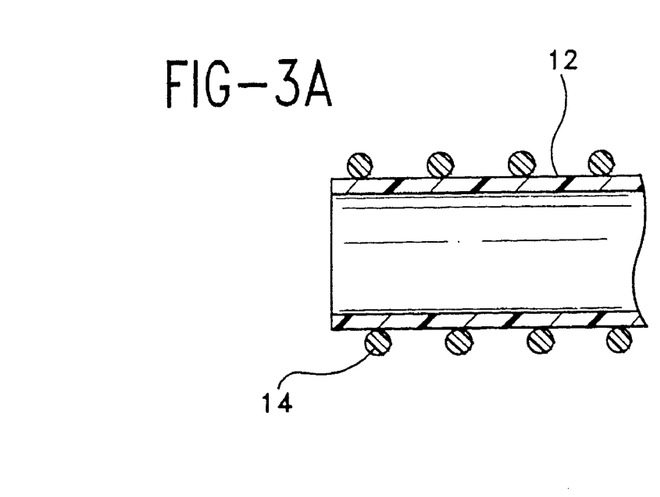
FIG. 3a illustrates the flexible implantable luminal device of the invention in longitudinal section, prior to fusing the filament and the tubular portions.
Figure 3B:
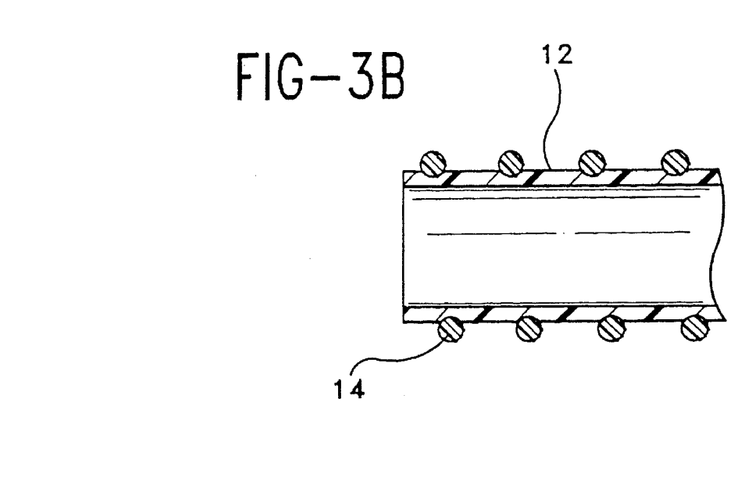
FIG. 3b illustrates the flexible implantable luminal device of the invention in longitudinal section, after the fusing of the filament and the tubular portions.

FIG. 2 shows a side view of an implantable luminal device according to the invention. FIGS. 3a and 3b show an implantable luminal device of the invention in longitudinal section and are related as two stages in the making of the implantable luminal device. FIG. 3a shows a tubular component around which has been helically wrapped a support component which includes a single filament. At this stage of the making, the filament has not been fused to the tube. FIG. 3b shows the same wrapped device as that shown in FIG. 3a except that the implantable luminal device has been fused according to the method of the invention so that the filament and the tube now form a unitary luminal device.

Although vascular and endovascular prostheses and grafts are among the more notable applications of the present invention, prostheses for use in other luminal body structures such as esophageal, intestinal, laryngeal, urethral, ureteral, and biliary structures, as well as various glandular ducts and conduits, and the like are contemplated. These are generally referred to herein collectively as "soft tissue" prostheses.

Among the vascular and endovascular prostheses which are specifically contemplated are arterio-venous (A-V) shunt grafts, such as those for dialysis applications, small diameter (3-10 mm) peripheral grafts, tapered grafts, aortic arch grafts, dilatable pediatric grafts, stents, and vein grafts.

Fluoropolymers are characterized by the fact that they are highly inert, paraffinic thermoplastic polymers that have all or some of the hydrogen replaced with fluorine. A variety of fluoropolymer compositions are useful according to the invention, including single and alloyed fluoropolymers manufactured according to processes known in the art. Such fluoropolymers include polymers of tetrafluoroethylene (PTFE), fluorinated ethylene-propylene copolymers (FEP), tetrafluoroethylene copolymers with ethylene, perfluoroalkoxytetrafluoroethylene (PFA), tetrafluoroethylene copolymers with perfluorovinyl ethers, and mixtures thereof. All of these are capable of being extruded, stretched and sintered. Much of the work on development of porous fluoroethylene polymers, and processes for producing porous tetrafluoroethylene polymer materials, have been disclosed in many U.S. patents.

The preferred fluoropolymer is PTFE. In general, any coagulated dispersion PTFE resin may be employed. Preferred PTFE resins include CD 123 and CD 509, available from Imperial Chemical Industries, Bayonne, N.J. Such PTFE resins generally are available as powders, having a median particle size in the range of about 500 μm, and an apparent density in the range of about 500 g/L.

Furthermore, the primary requisite of a suitable tetrafluoroethylene polymer resin for the process described above is a very high degree of crystallinity, preferably in the range of 95% or above, and correspondingly low amorphous content. Copolymers of tetrafluoroethylene which have defects in the crystalline structure that introduce a higher amorphous content are less preferred than are homopolymers.

The tubular portion of the prosthesis may be manufactured according to methods known in the art, preferably by extrusion methods. The temperature of extrusion is preferably below the crystalline melting point of the fluoropolymer.

The filament portion of the prosthesis may be made from a single fluoropolymer or an alloy of fluoropolymers selected from among those useful for making the tubular portion. The preferred fluoropolymer for the filament is polytetrafluoroethylene. The filament portion of the prosthesis may be made according to methods known in the art, preferably by extrusion methods and preferably extruded at a temperature below the crystalline melting point of the fluoropolymer. The filament portion is preferably a monofilament, but may be a braid of two or more smaller filaments.

The ability to form alloys of various fluoropolymers is well known in the art. U.S. Pat. No. 4,973,609, for example, describes the use of alloys of a variety of fluoropolymers, each individually possessing distinct physical characteristics, to yield materials possessing physical characteristics different from materials produced from single fluoropolymers. The alloy materials disclosed in this patent are described as capable of extrusion into tubular form.

In a preferred embodiment, the filament component and the tubing component are manufactured from the same fluoropolymer, most preferably PTFE. By employing the same fluoropolymer for each component, a unitary composite prosthesis may be formed by cosintering the components at an appropriate temperature. Since in this embodiment the melting point of each component is the same, the two components fuse when heated to a temperature in excess of the melting point. This allows the formation of a prosthesis without requiring additional means for causing the tubing and filament components to adhere to one another. Accordingly, adhesives, laminates or other physical means for maintaining the integrity of the composite prosthesis are rendered unnecessary, thus simplifying the structure of the prosthesis and the method of its manufacture.

The implantable composite prosthesis of the invention is formed from the filament component and the tube component by first expanding the tube by stretching in an axial and/or radial dimension. Then, the filament is wound around the tube in a helical configuration. The assembly is then controllably heated to a temperature above the crystalline melting point of the fluoropolymer to sinter the assembly, thereby fusing and uniting the assembly into a reinforced tubular structure for use as a vascular prosthesis.

A general procedure for producing porous fluoropolymer products by extrusion may be employed as is described in the art.

Initially, a dispersion of a fluoropolymer powder or coagulated dispersion, preferably highly crystalline PTFE, is mixed with a liquid lubricant and shaped. The lubricant should be capable of wetting the fluoropolymer surface, and of being removed by evaporation or extraction at a temperature below the crystalline melting point of the fluoropolymer.

Examples of suitable lubricants include liquid hydrocarbons such as solvent naphtha, white oil, etc.; aromatic hydrocarbons such as toluene, xylene, etc.; alcohols; ketones; esters; silicone oils; fluorocarbon oils; aqueous systems containing surfactants; and mixtures thereof. A particularly preferred lubricant is a synthetic isoparaffinic hydrocarbon available as ISOPAR® from Exxon Chemical Americas, Houston, Tex. ISOPAR® has a boiling point of about 154°–176° C.

The amount of lubricant to be used will vary according to the conditions of extrusion, the size of the desired product, and the nature and amount of the fluoropolymers and any additives included in the feedstock. The lubricant may be included in the feedstock in an amount of from about 10 wt. % to about 30 wt. %. Preferably, the lubricant is included in the feedstock in an amount of from about 15 wt. % to about 20 wt. %. Most preferably, the lubricant is included in the feedstock in an amount of about 17.5 wt. %.

The lubricant is then removed from the extrudate. The resulting dried extrudate may then be stretched at a high rate, usually at an elevated temperature which is nonetheless below the crystalline melting point of the tetrafluoroethylene polymer resin. While being held in the stretched state, the tetrafluoroethylene extrudate may be sintered by heating the stretched extrudate to a temperature above the crystalline melting point of the fluoropolymer. This process produces a material having a microstructure composed of nodes interconnected by very small fibers, also known as fibrils or microfibrils. This microstructure greatly increases the tensile strength of the tetrafluoroethylene polymer extrudate. Because of the node and fibril structure, the material is also substantially more porous than the original extrudate.

After extrusion, the fluoropolymer tube may be stretched or "expanded". Expansion is a term well known in the art and may be performed according to the methods known in the art. Generally, expansion involves stretching the extrudate in either the axial or the radial dimension, preferably involving simultaneous stretching in both the axial and radial dimensions. The expanding may be performed at temperatures ranging from about ambient temperature to an elevated temperature that is below the crystalline melting point of the fluoropolymer. The preferred temperature at which the expanding process may be performed is from about 100° C. to about 300° C., taking advantage of the fluoropolymer's thermoplastic properties. Preferably, the expanding is performed at a temperature of the extrudate of between about 150° C. and about 280° C. Most preferably, the temperature of the extrudate during the expanding step is between about 260° C. and about 270° C. The stretching ratio is commonly between about 20% and about 1200%. Preferably, the stretching ratio is between about 200% and about 1000%.

The expansion step is related to modification of several parameters governing the extruded fluoropolymer's behavior. At a gross level, the expansion directly increases the extrudate's diameter and length. Concomitantly, the thickness of the extrudate, i.e., the thickness at the wall of the extruded tube, is decreased. At a microscopic level the microstructure of the extrudate is also affected by the process of expansion. Expansion is well known in the art as a means of altering the size and number of pores in the extrudate. Given the applicability of the soft tissue prostheses, described herein, as vascular prostheses, the porosity of the tubes is preferably adjusted by expansion to improve the tube's behavior as functional replacements for vascular tissue. The pores are desirably at a size and number to optimize the endothelial ingrowth accompanying the formation of neointima upon implantation as a vascular replacement.

The temperature and particularly the rate of stretching greatly affect the porosity and tensile strength of the resulting material. Stretching performed at very high rates produces an increase in the strength of the resulting material. When an unsintered extrudate is stretched at lower rates, limited stretching occurs before fractures occur in the material. Furthermore, materials, produced through stretching at lower rates tend to have coarse microstructures and are mechanically weak. Extrudates expanded at both high temperatures and high stretch rates have a more homogeneous structure and a greater tensile strength than extrudates expanded at lower temperatures and lower stretch rates. Therefore, high stretch rates are believed to be necessary to produce strong materials, and both high stretch rates and high temperatures have been recommended to achieve high stretch ratios, homogeneous structures and strong materials.

The process discussed above does not generally produce PTFE materials having fine pores less than 2,000 Å in diameter. The process, however, can be modified to produce a PTFE material having such fine pores by first stretching the extrudate as discussed above, by then "free" sintering the extrudate by heating it above its crystalline melting point without subjecting the extrudate to tension by holding it in its stretched state, and by then stretching the extrudate a second time at a temperature below the crystalline melting point. The second stretching produces a PTFE material having uniform fine pores of between about 100 to about 1500 Å in diameter.

PTFE resin tubes having small pore size but high porosity can be produced by drawing a tubular PTFE extrudate in the lengthwise direction through a metal die and plug to perform the stretching operation. The thickness of the tube can be reduced to a level not previously possible by radially expanding the tube while simultaneously performing the sintering operation.

It has been confirmed clinically that when a structure composed of fibers and nodes is expressed in terms of pore sizes and porosities, or fiber lengths and nodular sizes, a polytetrafluoroethylene tubing, desirably has a pore size of from about 2 µm to about 30 µm. Pore sizes outside this range have been found to be less desirable. The porosity of tubing may be between about 50% and about 90%, expressed as a ratio of the density of the fluoropolymer product to the density of the untreated, source fluoropolymer. Preferably, the porosity of the tubing is between about 70% and about 85%. The fiber length of the extrudate is desirably between about 20 µm and about 110 µm. Preferably the fiber length is between about 20 µm and about 70 µm. The nodular size is preferably not more than about 20 µm. The wall thickness of the tubing depends on the overall diameter of the tubing and is generally selected to be in the range of from about 0.3 mm to about 2 mm. Preferably, the wall thickness is between about 0.3 mm and about 1 mm. It has been observed that tubing having the above-described physical dimensions exhibits a high patency rate without substantial occlusion by fibrin deposition.

The filament portion of the implantable prosthesis is produced separately by techniques known in the art, and is produced from a fluoropolymer material. The techniques useful for producing the fluoropolymer filament may include casting but preferably are extrusion techniques. Insofar as the filament is preferably extruded fluoropolymer, the fluoropolymer composition may be selected from among those fluoropolymers described above as useful for the extruded fluoropolymer tube portion. The conditions of extrusion are also preferably within the ranges provided above for the extrusion of the fluoropolymer tubes.

The filament may have any cross-sectional configuration, preferably a regular polygonal or rounded cross-section. The cross section of the filament is preferably selected to maximize the surface area through which it may be fused to the tubing. At the same time, the filament desirably minimizes the external irregularity or roughness of the unitary prosthesis by limiting the height of the filament above the tubing surface and by reducing angular ridges and clefts capable of injuring tissues when, for example, an intravascular prosthesis is drawn through a portion of a blood vessel. Accordingly, an acceptable filament cross section may be that of a semicircle or half moon. In this case, the flat portion of the filament would be fused to the tubing while the curved aspect would be exposed. In any case, the filament should have a substantially uniform cross-sectional area and configuration throughout its entire length, to avoid irregularities in the physical properties and behavior of the prosthesis.

One of the advantages of the prosthesis of the invention is that significant structural support is provided to the prosthesis by a highly biocompatible filament which does not completely cover the external surface of the tubing component. By avoiding complete coverage of the tubing, the prostheses of the invention avoid compromising the characteristics of porous fluoropolymer prostheses that permit successful implantation. Principally, this means that tissue ingrowth through the pores is not impeded to any significant degree, such ingrowth contributing substantially to prosthetic biocompatibility.

The filament component may be composed of a single filament wrapped helically about the central tubular portion. Alternatively, the filament component may be composed of two or more filaments wrapped independently about the central tube. Each filament may be composed of a single monofilament or may be composed of an arrangement of two or more smaller filament which are mutually intertwined, preferably in a regular braid or twist pattern. The preferred structure of each filament is a monofilament.

The cross-sectional width of the filament component is preferably selected to be as small as possible without compromising the structural support it provides to the underlying tubing. Generally, filament cross-sections in the range of from about 0.4 mm to about 6.5 mm have been found to be useful according to the invention when used to form prostheses of dimensions described elsewhere herein.

The filament or filaments may be wrapped around the central tube at an angle of winding, relative to the axis, of from about 30° to about less than 90°. Preferably, the angle of winding is from about 40° to about 80°. If more than one filament is wrapped about the tube, it is preferred that the angle of winding of each filament is equal to that of the others so that the filaments are substantially mutually parallel, i.e., non-overlapping. While it is preferred that the filaments create a pattern that is symmetrical, the filaments may be spaced at equal or unequal offsets on the circumference of the tube. Most preferably, the filaments will be affixed to the tube circumference at intervals of $2\pi/n$, where n=the number of filaments.

For practical reasons, the filament is wrapped around the tubing component while under tension, otherwise the filament might well slip and/or be displaced during manipulation prior to sintering. Accordingly, a tension is preferably exerted on the filament sufficient to avoid slippage while also being below a tension great enough to cause inordinate stresses in the composite structure. For example, an excessive tension might induce a torque in the prosthesis which, when implanted, could cause undesirable stresses at junctions with tissues, leading to leakages and other medical complications. It has been found that positive tensions of various amounts are useful according to the invention as long as the structure of the filament is not compromised. Practical amounts of tension can be determined in practice, based on considerations given to factors such as the fluoropolymer employed, the cross-sectional area of the filament and other physical factors.

Figure 4:
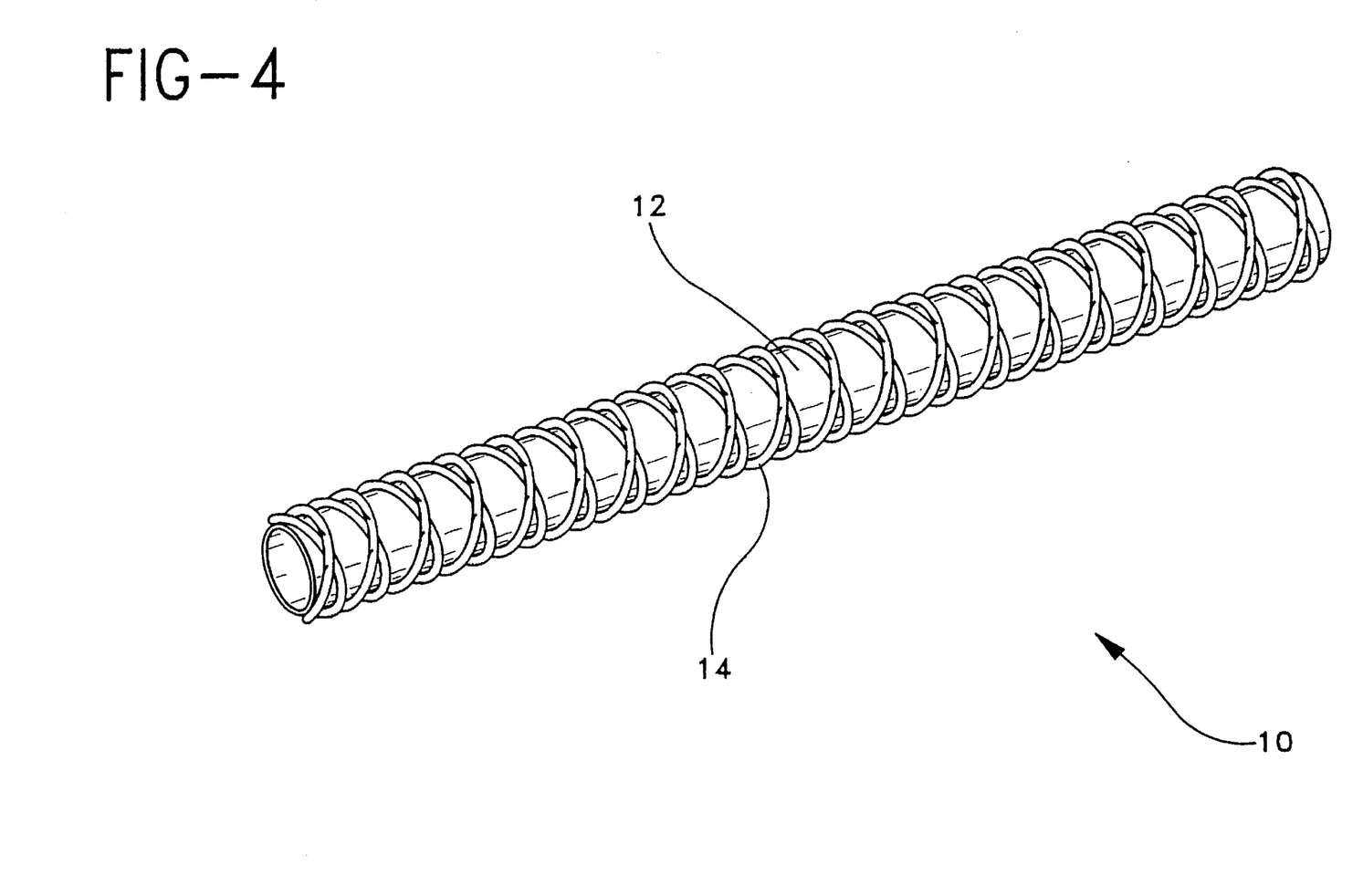
FIG. 4 illustrates an alternative embodiment of the flexible implantable luminal device of the invention, in perspective view.

In another embodiment, two or more filaments may be wrapped in substantially opposite winding orientations (e.g., right-handed and left-handed helices) such that the windings cross and overlap one another to form a substantially regular braid pattern. It is preferred in this embodiment that the filaments be wound at substantially identical angles of winding, although different winding angles are within the scope of the invention. FIG. 4 illustrates an embodiment of the invention in which the filament component includes a right handed helical filament and a left handed helical filament.

Whether wound in the same or opposite directions, the filaments may be wound sequentially or simultaneously, as desired. For example, the tube may be held without rotation and the filaments applied from revolving means moving around the tube. Alternatively, the tube may be rotated relative to a fixed filament depositing apparatus. Moreover, the tube and filament(s) may be counter-rotated, i.e., each is rotated in an opposite direction.

It is preferred that the support component be comprised of a single filament length wrapped helically around the tube for the length of the tube. Alternatively, the filament component may be discontinuous, being comprised of more than one segment of filament wrapped around the tube component. If more than one segment is employed, the segments may be wrapped sequentially, preferably so that the ends of each segment are juxtaposed with each adjacent segment end and preferably attaching each segment to the tube component so that segment ends are as close to each other in the longitudinal dimension as possible. Arrangements in which such segments are not matched in helical and/or longitudinal position are also contemplated as an embodiment of the invention. Alternatively, when more than one filament segment is used, the segments may overlap longitudinally such that two or more segments, whether of identical or non-identical lengths and/or diameters, may be fused to the tube component at any plane along the length of the tube.

The filament may be wound around the tube either prior to or after any stretching or expanding of the prosthesis. Preferably the filament is wound around a previously expanded tube. In addition, the filament may be wound around a tube that has or has not been sintered. It is preferred that the tube be sintered prior to wrapping the filament component. The composite structure is then re-sintered after wrapping to produce a unitary prosthesis.

Once the filament or filaments are wound around the tubular portion, the filaments are cosintered and fused to the exterior surface of the tube by means of heating the wrapped tube to a temperature in excess of the crystalline melting point of the fluoropolymer. In cases where PTFE is employed as the fluoropolymer, the sintering is generally performed using a temperature of between about 640° F. and about 700° F., preferably between about 640° F. and about 680° F. The assembly is heated for a period of from about 1 min. to about 60 min., preferably from about 15 min. to about 30 min., to effect the fusion of the filament(s) to the tube. These temperatures have been found to be useful for the sintering of filaments and for the cosintering of filament/tube composite articles.

The following Examples further illustrate the various features of the invention, and are not intended in any way to limit the scope of the invention, which is defined in the appended claims.

EXAMPLE 1

An undried extruded PTFE monofilament having a circular cross-section and a diameter of approximately 3 mm was then wound around a 6 mm internal diameter extruded PTFE tube that had been stretched, but was unsintered. The monofilament was secured in place by tying the sample off after winding.

The wrapped composite article was then placed in an oven and heated for approximately 25 minutes at 665° F. Upon cooling the filament was found to be fused to the tube, creating a unitary article.

The peel strength of the article exceeded 450 g as measured by an Instron Tensile Tester, Model 4500, available from Instron Instruments, Inc., Billirica, Mass. (This instrument was employed to determine peel strength in all relevant examples herein). Peel strength was determined using conventional methods known in the art.

EXAMPLE 2

An undried extruded PTFE monofilament having a circular cross-section and a diameter of approximately 0.74 mm was wrapped by hand around a stretched PTFE tube having a 6 mm outer diameter and a 0.8 mm wall thickness, that had been previously sintered. The assembly was then heated in an oven to 665° F. for 30 minutes to sinter and fuse the assembly.

Upon cooling, the peel strength of the fused assembly was 60.7±14 g, sustaining a maximum load of 78 g.

EXAMPLE 3

A length of PTFE monofilament having a diameter of about 0.74 mm (described in Example 2) was wrapped by hand around a stretched but unsintered PTFE tube having a 6 mm outer diameter and a 0.8 mm wall thickness. The assembly was then heated to 665° F. for 30 minutes to sinter and fuse the assembly.

Upon cooling, the peel strength of the fused assembly was 67±20 g, sustaining a maximum load of 86 g.

EXAMPLE 4

A length of PTFE monofilament having a diameter of 0.74 mm (described in Example 2) was wound around a segment of extruded PTFE graft, having an 8 mm outer diameter and a 1.0 mm wall thickness, which had been expanded and sintered by conventional methods. The winding was performed on a production lathe using tension provided through the application of a 50 g weight. The assembly was then heated at 700° F. for 30 minutes.

Upon cooling, the peel strength of the fused assembly was 76 g with a load at peak of 100 g.

EXAMPLE 5

A length of PTFE monofilament having a diameter of 0.74 mm (described in Example 2) was wound around a segment of expanded and sintered PTFE graft, having a 6 mm outer diameter and a 0.8 mm wall thickness. The winding was performed on a production lathe using tension provided through the application of a 50 g weight. The assembly was then heated at 665° F. for 30 minutes.

Upon cooling, the peel strength of the fused assembly was 68 g, with a load at peak of 95 g.

EXAMPLE 6

To demonstrate the superior physical characteristics of tubular prostheses manufactured according to the invention, various prostheses were tested for kink resistance as shown below.

The relative kink resistance of each prosthesis was measured in a dry, unpressurized condition. Each specimen was manipulated to form a substantially planar loop such that the ends of the prosthesis were facing away from one another. The ends were then slowly pulled past one another to gradually reduce the diameter of the loop, until the first evidence of kinking occurred. The inside loop diameter at this point is termed "kink diameter". This procedure was performed over a metric rule so that the inside loop diameter could be continuously monitored. A measure of relative kink resistance was established as follows:

$$\text{Kink Ratio} = \frac{\text{Kink Diameter (mm)}}{\text{Prosthesis Internal Diameter (mm)}}$$

PTFE tubes were extruded according to methods known in the art. Four sizes of tubes were produced as follows:

4 mm Internal Diameter; 0.6 mm Wall Thickness ("Thin Wall")

4 mm Internal Diameter; 0.85 mm Wall Thickness ("Standard Wall")

10 mm Internal Diameter; 0.6 mm Wall Thickness ("Thin Wall")

10 mm Internal Diameter; 0.85 mm Wall Thickness ("Standard Wall")

Samples of the 4 mm and 10 mm thin walled tubes were then modified by adding extruded PTFE helical support filaments according to the invention. The filaments had a diameter of 0.74 mm and were fused to the tube by heating at 685° F. for 15 minutes.

Data obtained from kink tests on each type of tube are described in Table 1 below. Three samples of each tube type were tested, designated A, B and C.

TABLE 1

|  | Kink Diameter, mm | | | |
| --- | --- | --- | --- | --- |
|  | A | B | C | Kink Ratio, Avq. |
| 4 mm, thin wall | 10 | 8 | 7 | 2.1 |
| 4 mm, standard wall | 1 | 1 | 1 | 0.3 |
| 4 mm, thin wall supported | * | * | * | N/A |
| 10 mm, thin wall | ** | ** | ** | N/A |
| 10 mm, standard | 12 | 13 | 9 | 1.1 |
| 10 mm, thin wall supported | * | * | * | N/A |

\* = Tube exhibited no measurable kink
\*\* = Tube kinked so quickly no useful values could be obtained.

It is clear from the data shown in Table 1, above, that, under the described conditions, the physical characteristics of both 4 mm and 10 mm internal diameter are greatly enhanced by providing helical support in accordance with the invention. While for each tube internal diameter, the resistance to kinking is increased by increasing the wall thickness, the provision of support according to the invention provides significantly greater kink resistance. For practical purposes, the tubes manufactured according to the invention are essentially "kink-proof" insofar as no kink was able to be produced even when kink diameter was decreased to below 1 mm.

Although illustrative embodiments of the present invention have been described herein, it is to be understood that the invention is not limited to those precise embodiments, and that various other changes and modifications may be effected therein by one skilled in the art, without departing from the scope or spirit of the invention.

What is claimed is:

1. An implantable luminal device, comprising:

an elongate flexible tube of a first fluoropolymer, said tube having a node/fiber microstructure, which is sufficiently porous to permit tissue ingrowth when implanted in the body; and a support component comprising at least one flexible filament of a second fluoropolymer, said at least one filament wrapped helically around an external wall of the tube;

wherein said first and second fluoropolymers have substantially the same crystalline melting point, said flexible filament being cosintered with and fused to said exterior wall of said tube.

2. The luminal device of claim 1, wherein said fluoropolymers are independently selected from the group consisting of polymers of tetrafluoroethylene, fluorinated ethylene-propylene copolymers, tetrafluoroethylene copolymers with ethylene, tetrafluoroethylene copolymers with perfluorovinyl ethers, and mixtures thereof.

3. The luminal device of claim 1, wherein said first and second fluoropolymers are identical.

4. The luminal device of claim 3, wherein said first and second fluoropolymers comprise polytetrafluoroethylene.

5. The luminal device of claim 1, wherein said tube is an extruded tube.

6. The luminal device of claim 5, wherein said extruded tube is an expanded tube.

7. The luminal device of claim 1, wherein said at least one filament is wrapped at an angle of from about 30° to about 90° relative to a longitudinal axis of said elongate tube.

8. The luminal device of claim 1, further including said support component being partially dried.

9. The luminal device of claim 1, further including said support component being partially dried.

10. The luminal device of claim 1, wherein said support component comprises two or more filaments wrapped helically around the external wall of the tube.

11. The luminal device of claim 10, wherein said filaments are wrapped helically in a substantially mutually parallel orientation.

12. The luminal device of claim 10, wherein said filaments are wrapped helically in a substantially opposing orientation.

13. The luminal device of claim 1, wherein said at least one filament is substantially continuous along the length of the device.

14. The luminal device of claim 1, wherein said at least one filament is discontinuous along the length of the device.

\* \* \* \* \*